United States Patent [19]
Yoshida

[11] Patent Number: 5,187,573
[45] Date of Patent: Feb. 16, 1993

[54] INSPECTION METHOD AND APPARATUS
[75] Inventor: Hajime Yoshida, Tokyo, Japan
[73] Assignee: Hajime Industries, Tokyo, Japan
[21] Appl. No.: 757,543
[22] Filed: Sep. 11, 1991
[30] Foreign Application Priority Data
   Sep. 19, 1990 [JP] Japan ................................. 2-249711
[51] Int. Cl.[5] ............................................. H04N 7/18
[52] U.S. Cl. ................................ 358/106; 250/223 B; 358/101
[58] Field of Search ................. 358/101, 106; 382/8; 250/223 B

[56] References Cited
   U.S. PATENT DOCUMENTS 4,691,231  9/1987  Fitzmorris ..................... 358/106
   4,948,956  8/1990  Fukuchi ...................... 250/223 B
   5,007,096  4/1991  Yoshida ......................... 358/101

Primary Examiner—Howard W. Britton
Attorney, Agent, or Firm—Bauer & Schaffer

[57] ABSTRACT

An image of the inspected object, irradiated by a light, is picked by a video camera and a video signal therefrom is processed by an electronic processor. A pattern judging window is setup on the inspected object to thereby judge whether a pattern exists on the object, and when it is judged that there is no pattern a plurality of inspection windows are set up to thereby perform a predetermined defect inspection on portions of the inspected object within the plurality of windows. A pattern discrimination window is setup on the inspected object when it is judged that there exists a pattern so as to discriminate the kind of pattern, and either setting up the inspection window or another inspection window depending on the kind of pattern so discriminated.

22 Claims, 7 Drawing Sheets

FIG. 6A1
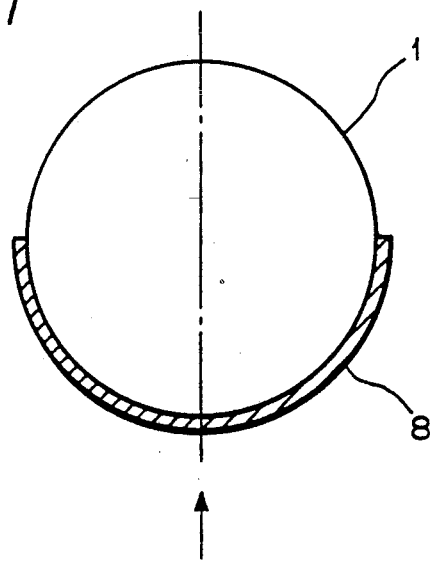
FIG. 6A2
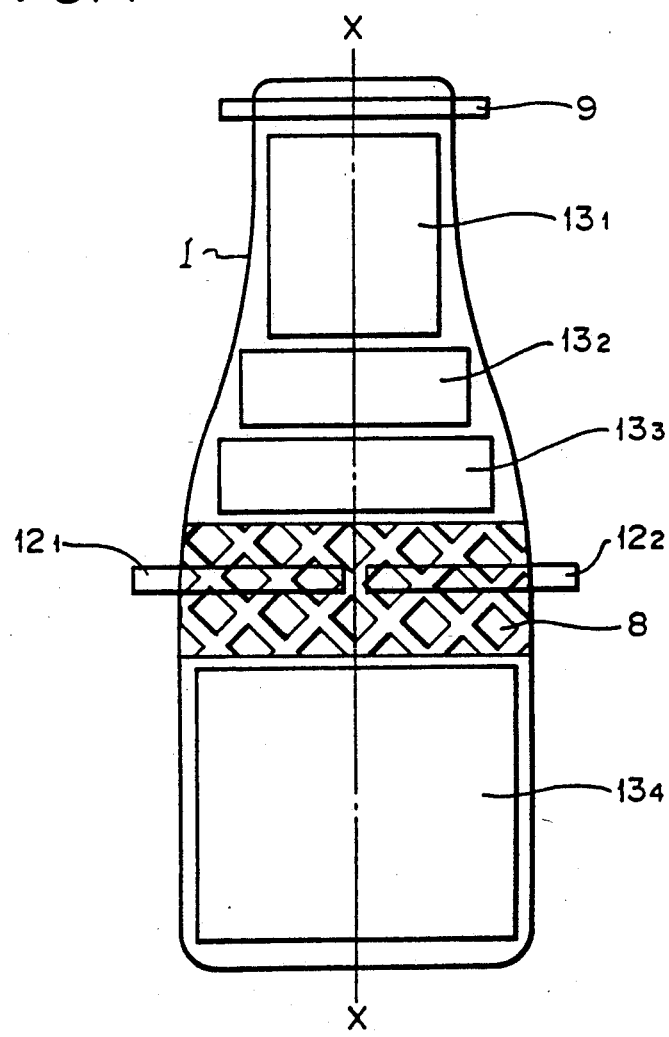

FIG. 6B1
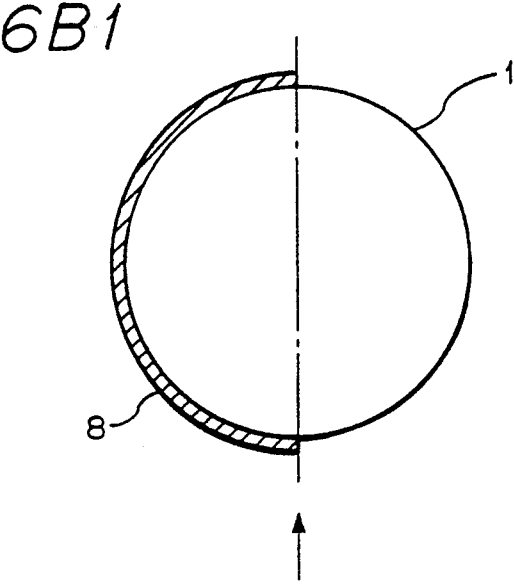
FIG. 6B2
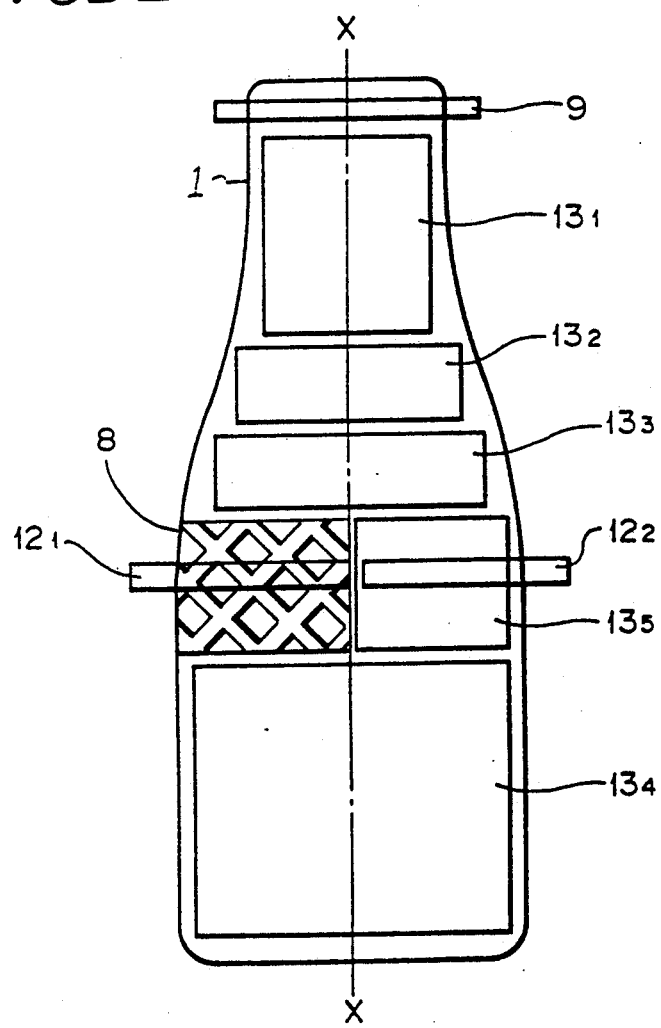

FIG. 6C1
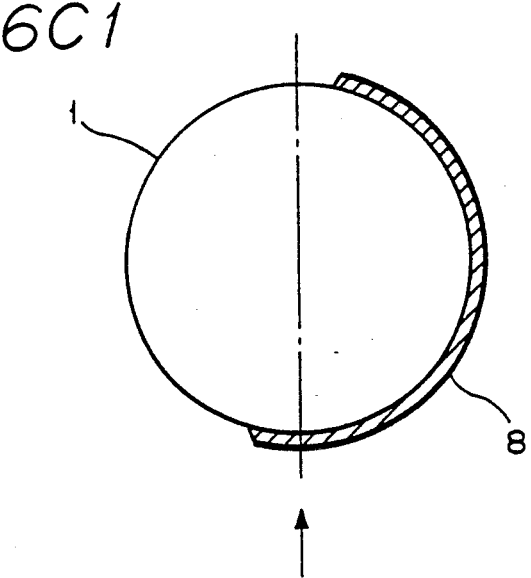
FIG. 6C2
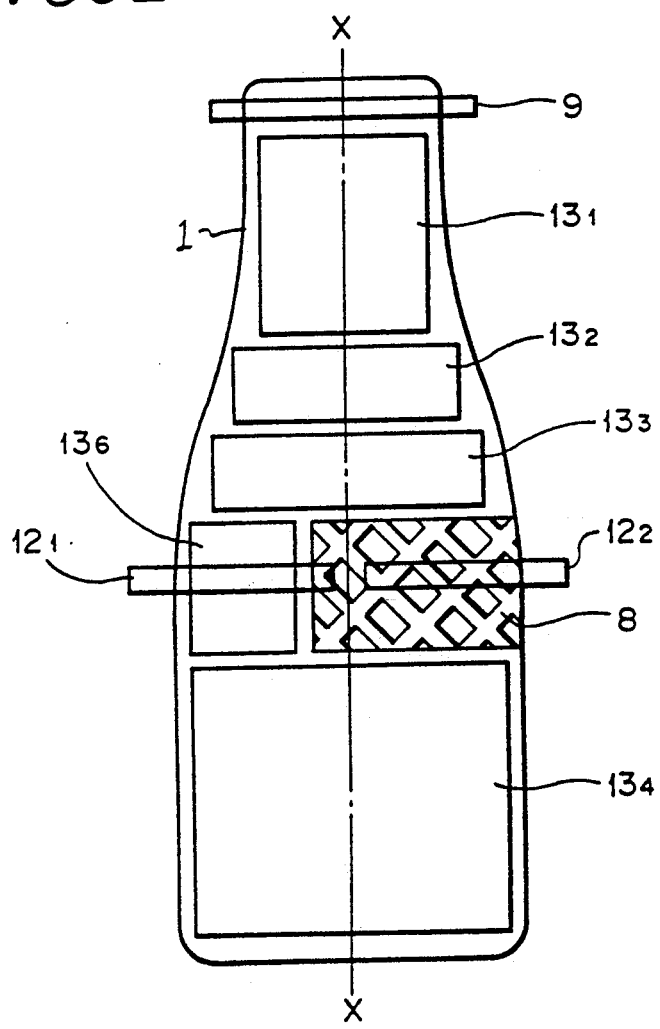

INSPECTION METHOD AND APPARATUS

FIELD OF THE INVENTION

The present invention relates generally to a method and apparatus for the inspection of containers or the like and particularly for the inspection of containers using a video camera or the like as an image sensor and an electronic processor.

BACKGROUND OF THE INVENTION

Description of the Prior Art

It is the conventional practice to manually conduct visual inspection of containers during their production, processing or completion after filling, in order to detect defects and maintain quality inspection. In the recent years, in order to create labor savings or for automation as a means of overcoming labor shortage, it is the trend to install automatic inspection apparatus using video camera and an electronic processor to replace manual inspection.

As an example, bottles or the like formed by plastic or glass are widely used as the beverage containers. Often such containers break or leak due to improper processing during the manufacturing of the containers of their handling during transit. Carelessness in handling and mishaps during the manufacturing process of containers result in such damage to the containers that they create a defective condition during the subsequent filling process and/or the capping of the containers. Therefore, at the present time a large number of people are required to conduct visual inspection at the various stages, starting with the beverage container manufacturing, the container washing, filling, capping as well as the ultimate packaging. Accordingly, in order to replace the manual processing, the installation of automatic inspection apparatuses that utilize a video camera and an electronic processor has become the practice by which faulty containers are automatically rejected.

Such arrangements are not only needed for beverage containers, but also required during the production and filling of various other types of products.

One example of such above mentioned container or commodity inspection apparatus of the prior art is explained with reference with FIG. 1 to FIG. 3.

FIG. 1 schematically shows the structure of a container inspection apparatus in which a container made of transparent material such as glass, plastics or the like, is irradiated by a lighting device 2 such as a light source, i.e.: a lamp or the like. A light diffuser place 3 is placed between the lighting device 2 and container 1 in order to uniformly diffuse the light from light source 2. A video camera 4 used as an image sensor picks up the image of container 1, and passes the image to an electronic processor 5 which is composed of a computer or the like. A monitor M1, to which the output from the video camera 4 and the electronic processor 5 are supplied so that the respective windows 6 and $7_1$-$7_4$ are shaped and display thereon the image of container 1 as will be described later.

In this apparatus, the light passes through a transparent container 1 and is caught by the video camera 4, which video output is processed by electronic processor 5 so that the existence or not of defects on the container 1 is detected. For containers that are of an opaque nature the system will catch the reflected light and a similar inspection can be conducted.

The block diagram of FIG. 2 shows the composition and function of the electronic processor 5 in the inspection apparatus of the prior are, and the schematic diagram of FIG. 3 shows the positions of the respective image windows relative to the container 1. As shown in FIGS. 2 and 3, the output video signal of video camera 4, first provides a positioning window 6 set at the neck portion of container 1 and determines the center axis x—x of container 1 in the electronic processing circuit 6A. In other words, both side edges of the neck portion of container 1 is detected within window 6 from which edges the center axis x—x of container 1 is determined. The purpose in determining the center axis x—x is to accurately setup the positions of the remaining inspection windowns relative to container 1. In other words, when the container 1 is assumed to be of symmetrical shape with respect to the center axis x—x, the respective inspection windows can be setup to be also symmetrically shaped with respect to the center axis x—x of container 1.

The above mentioned inspection windows are shown in FIG. 2 and 3 by the numerals $7_1$, $7_2$, $7_3$ and $7_4$. If four inspection windows $7_1$ to $7_4$ are employed and the shapes of the respective inspection window $7_1$ to $7_4$ may be adjusted slightly to cope with any change in the shape of container 1. Further, variations in light transmission, due to the change in the diameter of the container 1 dependent on its position can be accommodated by varying the position and shape of the inspection windows $7_1$ to $7_4$ upon electronic processing. The existence of any defects in the container 1 observed within the four inspection windows $7_1$ to $7_4$ are simultaneously judged at a judgment processing circuit 7A.

The advantage of providing four inspection windows $7_1$ to $7_4$ for one container 1 lies in the fact that if there is any variance in the shape of container 1 such as (when the diameter of container 1 changes, or when the shape of its neck changes, etc), it will be easy to respond thereto by making a slight changes in the dimension of shape of only the corresponding windows $7_1$ to $7_4$. In order to respond to the changes of the light transmission due to the differences in the diameter of the container the respective windows $7_1$ to $7_4$ can be set up within the electronic processing with separate sensitives. When a design or literal arrangement of lines or the like exists on a part of container 1 (hereafter called a pattern) it is difficult to detect any defect therein and that area to be exempt from inspection.

In the inspection apparatus above described, there is generally no need to conduct inspection of the pattern 8 portion of container 1. However, such pattern referred to by the numeral 8 generally exists around the entire outer circumference of the container 1 body. In many cases such pattern 8 is formed only about half the circumference. In this case, it is necessary to judge the good or bad of the portions other than the pattern 8. By the conventional apparatuses, it was impossible to make this judgment.

OBJECTS AND SUMMARY OF THE INVENTION

Accordingly, it is an object of the present invention to provide a novel inspection apparatus that entirely removes the drawbacks and faults of the above described prior art apparatus.

According to another aspect of the present invention, there is provided an inspection method for detecting the existence of a defect on an object in which an image of the inspected object irradiated by a light is picked by a video camera and a video signal therefrom is processed by an electronic processor comprising the setups of:

setting up a pattern judging window for the inspected object to thereby judge whether or not there exists a pattern in said inspected object;

setting up a plurality of inspection windows when it is judged that there is no pattern in said inspected object to thereby perform a predetermined defect inspection on portions of said inspected object within said plurality of inspection windows;

setting up a pattern discrimination window in said inspected object when it is judged that there exists a pattern on said inspected object to thereby discriminate the kind of said pattern; and either setting up said inspection window or another inspection window dependent on the kind of said pattern discriminated.

According to another aspect of the present invention, there is provided an inspection apparatus for detecting existence of a defect in an inspected object in which an image of the inspected object irradiated by a light is picked by a video camera and a video signal therefrom is processed by an electronic processor comprising:

first means for setting up a pattern judging window to thereby judge whether or not there exists a pattern on said inspected object;

second means for setting up a plurality of inspection windows when it is judged that there is no pattern in said inspected object to thereby perform a predetermined defect inspection on portions of said inspected object within each said plurality of inspection windows;

third means for setting up a pattern discrimination window on said inspected object when it is judged that there exists a pattern on said inspected object to thereby discriminate a kind of said pattern; and fourth means for either setting up the inspection windows or another inspection window dependent on the kind of said pattern discriminated.

A better understanding of the objects, features and advantages of the invention can be gained from a consideration of the following detailed description of the preferred embodiments thereof, in conjunction with the figures of the accompanying drawings through which like references designate the same and similar elements.

BRIEF DESCRIPTION OF THE DRAWINGS

FIGS. 5A, 5B and FIGS. 6A1, 6B1, 6C1 as well as 6A2, 6B2 and 6C2 are schematic diagrams respectively illustrating the functioning of the present invention.

DETAILED DESCRIPTION OF THE PREFERRED EMBODIMENTS

Figure 1:
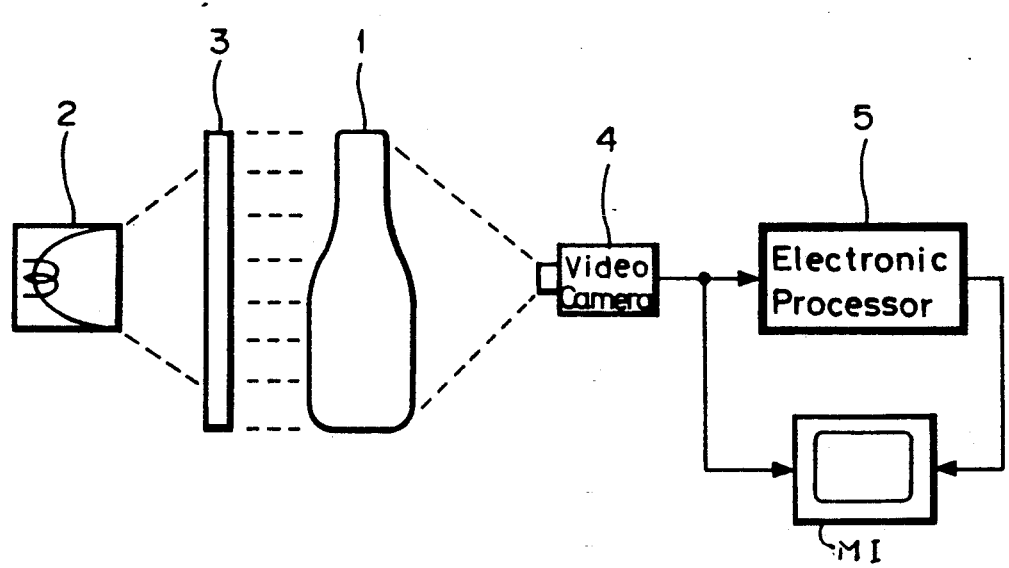
FIG. 1 is a schematic diagram of an example of a conventional fault inspection system to which the present invention is applied.
Figure 4:
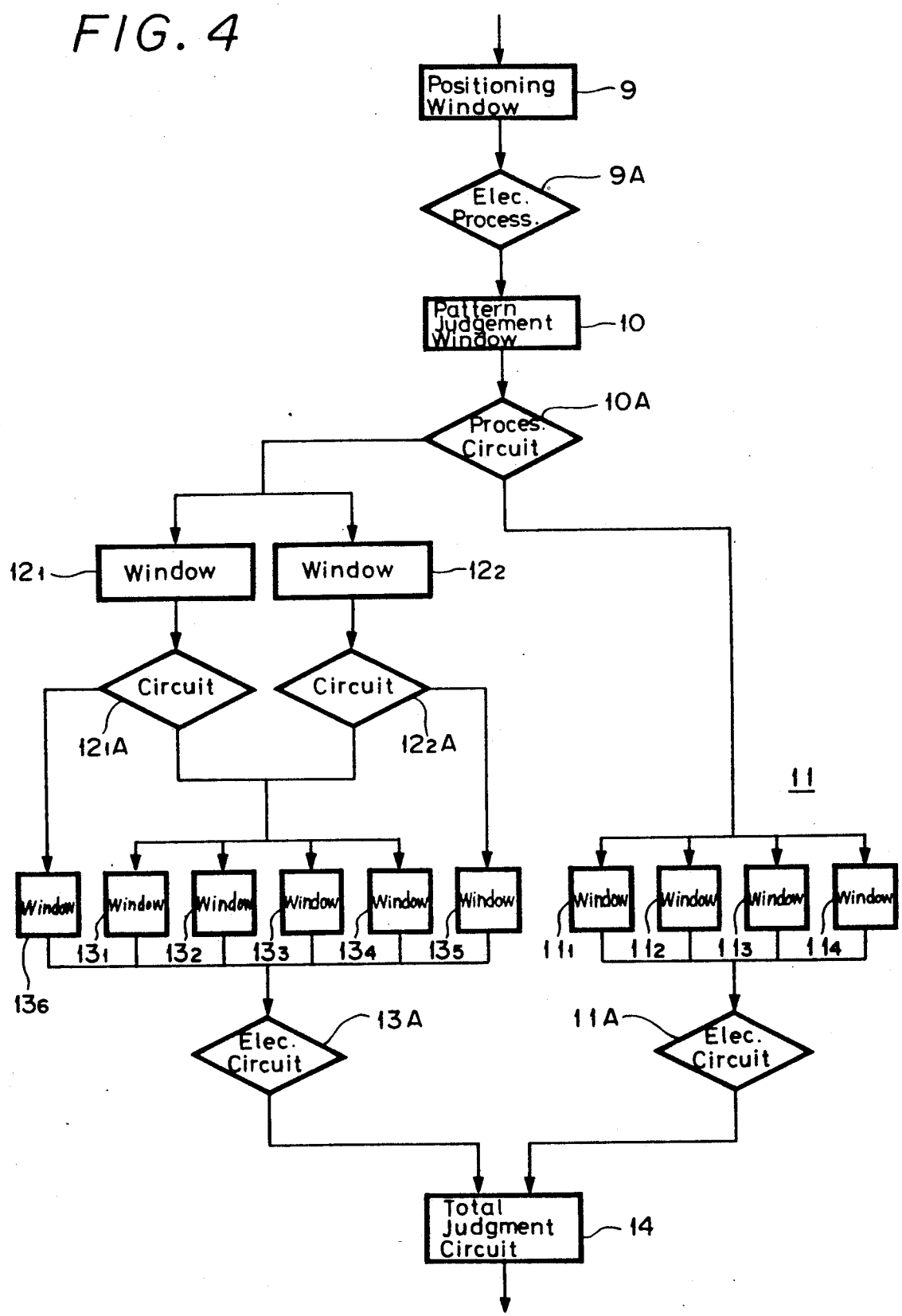
FIG. 4 is a block diagram showing the main structure and function of an embodiment of the present invention.

An embodiment of the present invention as seen in FIG. 4 to FIG. 6 is applied to the system having a similar structure to that shown in FIG. 1.

FIG. 4 is a block diagram that shows each of the structure and functions of the electronic process 5.

First, based on the video signal from the video camera 4 (refer to FIG. 1), a positioning window 9 is setup at the neck portion of container 1, and then based on this window 9, the center axis x—x of container 1 is sought by electronic process 9A. Next, a pattern judgment window 10 determining if there exists a pattern 8 on container 1, is setup.

Figure 5A:
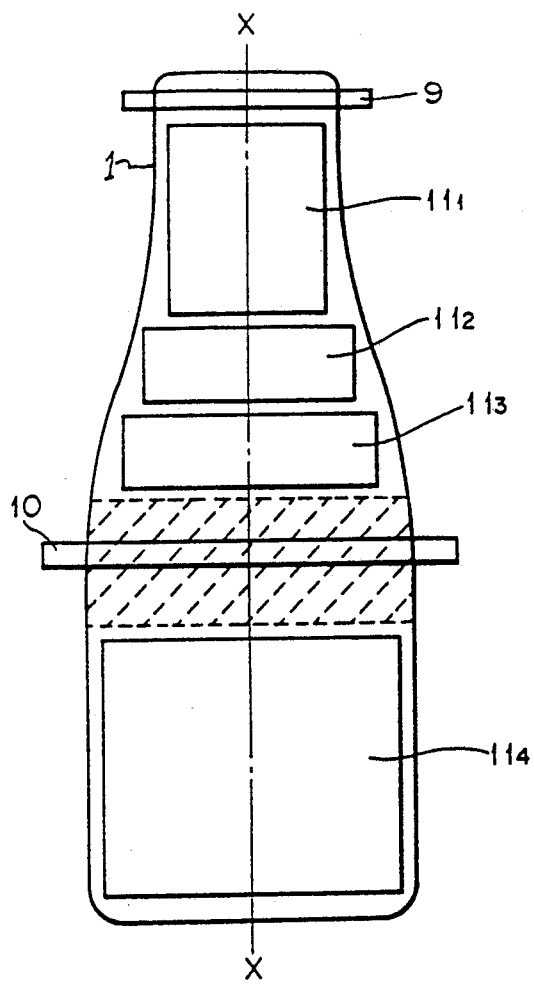
Figure 5B:
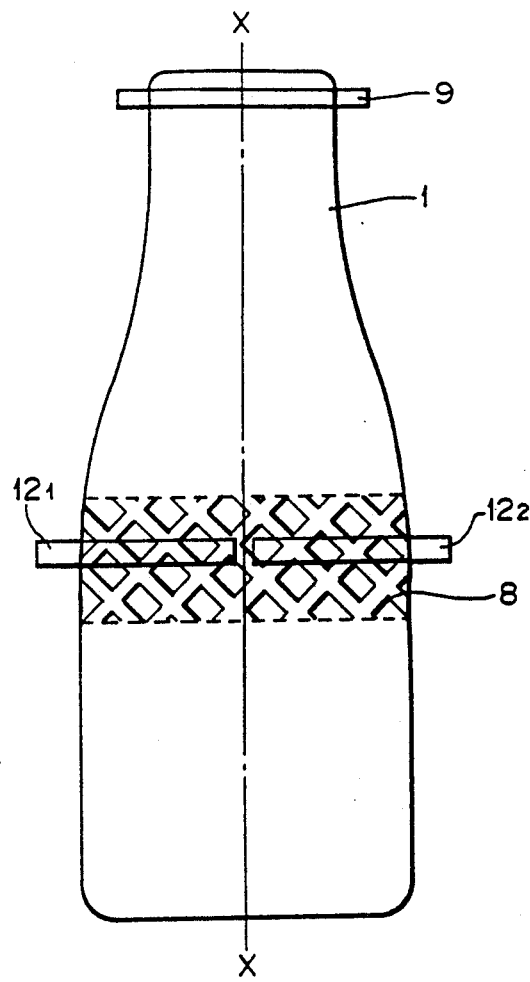

Now, in order to have an easier understanding of operation of the present invention, the conditions of the respective windows are shown in FIGS. 5A and 5B.

The pattern judgement window 10 is setup as seen in FIG. 5A at the zone that is exempt from inspection in the conventional example and the existence or not of a pattern 8 is detected by the brightness of this window. In other words, when there is pattern 8 on the outer surface of the container 1, the irradiated light is diffused and the light that arrives at the video camera 4 is correspondingly weakened. Therefore, by checking the intensity of the light from the area occupied by the patter 8, its existence is easily detected.

Based on the detection of pattern 8 a brightness processing circuit 10A is used to select the positions, shapes and so on of the other areas of the containers for which corresponding inspection windows are next setup. That is, the processing circuit 10A operates such that when there exists a pattern 8 the portion of the container is exempted from the zone of inspection. When however, there no pattern exists, the processing circuit selects a separate window that does not exempt the area of the container from inspection.

In the present invention, when there is no pattern 8 on the container 1, the electronic processor circuit 10A detects that such portion is bright and the electronic processor circuit 10A selectively sets up the inspection window 11. This inspection window 11, in this case similar to the conventional example, is comprised of 4 windows $11_1$, $11_2$, $11_3$, $11_4$. The difference with regard to the conventional system is that as shown on FIG. 5A, the shape of window $11_4$ is different from the conventional window $7_4$ in that it is large enough to include the pattern 8. This has the purpose of also including this portion in the inspection area when it is determined that there is no pattern. Thus, the defects of container 1 within the windows $11_1$–$11_4$ are totally detected by defect processing circuit 11A in the same manner as in the conventional example.

On the other hand, when a pattern 8 exists within window 10 and the electronic processor circuit 10A determines the portion of container to be dark, the processor circuit 10A selectively sets up a pattern judgment window 12 instead of window 11, in order to determine the shape, etc. of pattern 8. This window 12, as shown in FIG. 5B is formed by a pair of windows $12_1$, $12_2$ arranged adjacent to each other in the lateral direction. In other words, as shown in FIG. 5B, one window $12_1$ is setup on one side of the pattern 8 portion which may be the left half of the container, while the other window $12_2$ is setup at the right half of the pattern and container.

In general, since the pattern 8 on the container 1 varies considerably, (for example sometimes being on the entire outer circumference and sometimes only involving a partial area of container 1). In FIGS. 6A1, 6B1 and 6C1, the instance where roughly half of the circumference of container 1 is covered by the pattern 8 shall be explained.

When the video camera 4 picks up the container 1, the image of pattern 8, varies depending upon the angle of the container 1 in its rotation direction relative to the camera. This is, for instance due to the fact that the inspection is conducted while the container 1 is being transferred on a belt conveyor (not shown), so that the rotation angle of the pattern 8 on the container 1 is not always in the same position. FIGS. 6A1, 6B1 and 6C1 illustrate three cases with different rotation angles in der to explain the operation.

Figure 2:
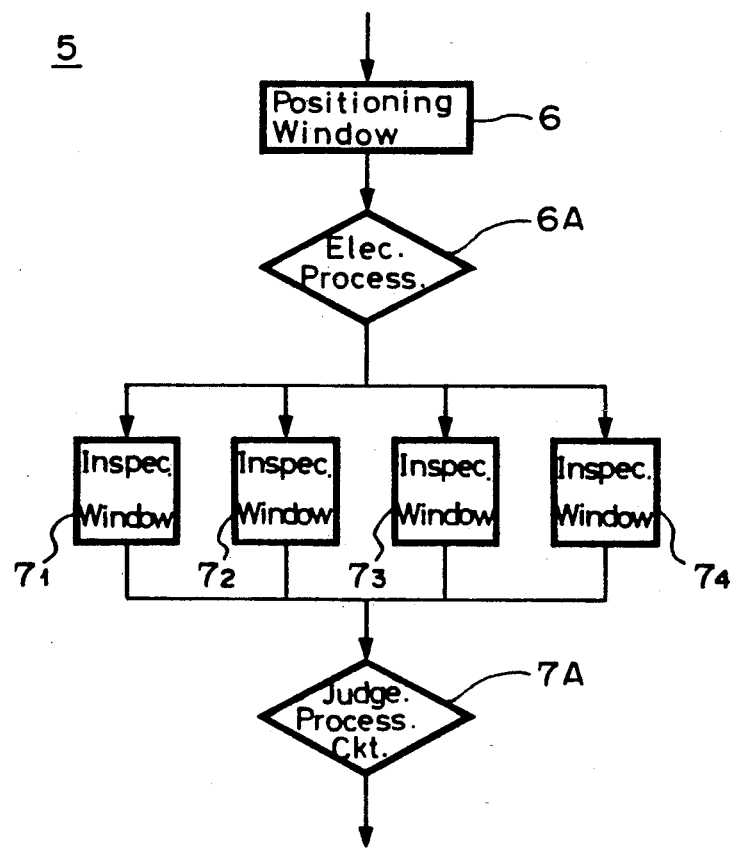
FIG. 2 is a block diagram showing the electronic process in FIG. 1.
Figure 3:
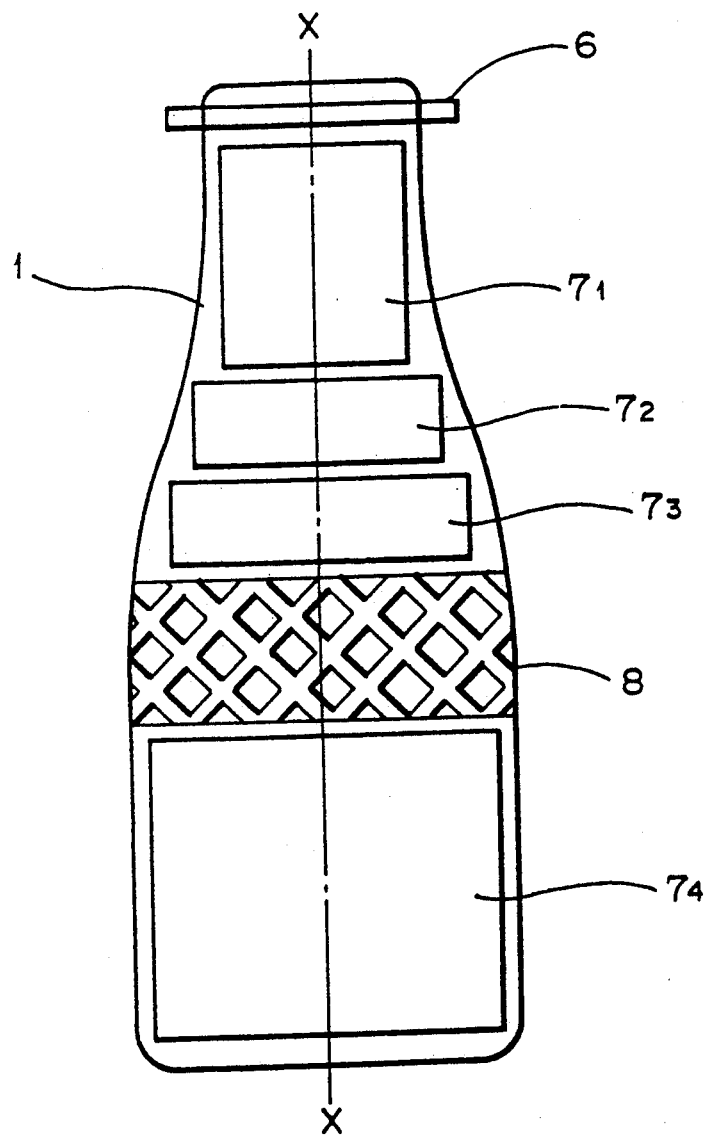
FIG. 3 is a schematic diagram to explain the function of an example of the prior art.

In the case of FIGS. 6A1 and 6A2, since both windows $12_1$, $12_2$ equally contain pattern 8, respective electronic processors or brightness detection and dimension processing circuits $12_1A$ and $12_2A$ (FIG. 4) will sense that the entire inner areas of both windows $12_1$ and $12_2$ are dark and as shown on FIG. 6A2 will setup the 4 inspection windows $13_1$, $13_2$, $13_3$, $13_4$. In this case, the portion of the container 1 containing pattern 8 is eliminated from inspection and the respective inspection windows $13_1$–$13_4$ act as those $7_1$ and $7_4$, as shown on FIG. 3. A defect detection processor circuit or electronic processing circuit 13A (FIG. 4) equally processes the defect detection on container 1 within the 4 respective windows $13_1$–$13_4$ in the same manner as in the conventional cases.

FIG. 6B1 and 6B2 show the case wherein the pattern 8 is only at the left side of container 1. Here one window $12_1$ includes the pattern 8 so that its electronic processor circuit $12_1A$ senses that the area within window $12_1$ is dark, and sets up the above-mentioned inspection windows $13_1$, $13_2$, $13_3$, $13_4$ while at the same time, since thee is no patter 8 existing within window $12_2$, its electronic processor circuit $12_2A$ senses that the area within window $12_2$ is bright and hence as shown on FIG. 6B2, in addition to the 4 windows $13_1$–$13_4$, sets up an inspection window $13_6$ at the portion of container 1 where window $12_2$ exists. In this case, the inspection windows $13_1$–$13_4$ supplemented with the inspection window $13_6$ with this inspection window $13_5$, the right side of container 1 which does not have pattern 8 can be inspected; a function that was impossible with the conventional apparatus. Thus, all the defects within the five windows $13_1$–$13_4$ can be totally processed by the defect detection processor circuit or the electronic processing circuit 13A.

FIGS. 6C1 and 6C2 illustrate the case where pattern 8 is substantially on the right side of the container 1 while a small amount of the pattern 8 protrudes onto the left side over the center axis x—x. Here, the electronic processor circuit $12_2A$ of course senses that the area within window $12_2$ is dark and sets up the inspection windows $13_1$, $13_2$, $13_3$, $13_4$ similarly to the case shown on FIG. 6A2. At the same time, electronic processor circuit $12_1A$ judges that only a bright portion partially exists within window $12_1$, measures the dimension of the left side portion of window $12_1$, where there is no pattern 8, and consequently also sets up an inspection window $13_6$ in an appropriate and corresponding shape as shown on FIG. 6C2. At this time, the electronic processor circuit 13A processes the defects within the five windows $13_1$ to $13_4$ and the enlarged window $13_6$ in the same manner as previously described.

In FIG. 6B1, if the right edge of patter 8 protrudes on to the right side over the center axis x—x a window $13_5$ of corresponding dimension will be set up and the faults within it measured in the same manner as described.

The outputs from the electronic processor circuits 11A and 13A are input to a total judgment circuit 14. The total judgment circuit 14 makes a final information output signal from the judgment outputs of the electronic processor circuits 11A and 13A. This final output signal may be supplied to a host computer and to a printer for recording, or used to control a conveying system and/or other device or devices. It is needless to say that the judgment outputs from electronic circuits 11A and 13A may also be directly used if desired at times. Also, as shown on FIG. 1, the outputs from video camera 4 as well as electronic processor 5, may be supplied to the monitor M1 so that the respective windows can be displayed thereon as overlapped on the image of container 1, then the apparatus function conditions can be easily verified.

As so above described, the inspection apparatus of the present invention can flexibly respond to the existence of patterns, lettered lines or other different appearances of the patterns due to the varied angles of rotation of the containers. An example with containers was cited, but it is apparent that the main concept of the present invention can be applied to other products and commodities. That is to say that it is of course applicable to flexibly structures composed without being bound by the sample embodiments as cited, by arrangements of the number of windows as well as by the number of processing to such numbers of windows.

Further, although defect inspection depending upon rectangular shaped windows has been explained, the window shapes may be freely composed, as may alternative methods for the electronic processing. Judgment of the shapes within the windows or the appropriate processing method that respond to the purposes such as measurement of specific areas may be adopted as mentioned above.

Further, when the pattern 8 on the container 1 is not one as explained above, but is plural in number, inspection may still be effected by setting up a plural number of windows as the pattern positions in the same number. The processing conducted against pattern judgment window 10 as shown on FIG. 4 in the same manner to these plural numbered pattern judgment windows, shall suffice.

Also, in response to the results of the processing circuits 11A, 13A, as shown on FIG. 4, setup of pattern judgment window 10 and the consecutive processing is such same manner may be added. It is further needless to say that such processing may be conducted in a multi consecutive manner.

When plural numbers of windows were setup in the inspection apparatus of the prior art, the functions were in parallel with exclusive processing conducted, while the setup conditions were constant without flexibility. Against such, the functions of the multi windows of the present invention are setup in a manner of casual relations respectively to each other. That is, in accordance to the results of specific electronic processing to any specific window, the next setup window is selected in order to form a consolidated flow of inspection processing.

Once the windows and electronic processing methods are established so that the response to variable condition changes is secured, the apparatus automatically judges in compliance with the physical or optical variations of the inspected object, so that a flexible and appropriate consolidated judgement can be made. This is a great advantage of the invention which does not exist with inspection apparatus of the prior art. Therefore, the present invention as a wide application range. Inspection of products having many variations is widened while the setup permits manipulations making many are exempt from inspection so that an extremely practical use is available.

It should be understood that the above description is presented by way of example on the preferred embodiments of the invention and it will be apparent that many modifications and variations thereof could be effected by one with ordinary skill in the art without departing from the spirit and scope of the novel concepts of the invention so that the scope of the invention should be determined only by the appended claims.

I claim as my invention:

1. An inspection method for detecting existence or not of a defect on an inspected object in which an image of the inspected object irradiated by a light is picked by a video camera and a video signal therefrom is processed by an electronic processor comprising the steps of:
   a) setting up a pattern judging window on said inspected object to thereby judge whether or not there exists a pattern on said inspected object;
   b) setting up a plurality of inspection windows when it is judged that there is no pattern on said inspected object to thereby perform a predetermined defect inspection on portions of said inspected object within said plurality of inspection windows;
   c) setting up a pattern discrimination window on said inspected object when it is judged that there exists a pattern on said inspected object to thereby discriminate a kind of said pattern; and
   d) either setting up said discrimination window or another inspection window dependent on the kind of said pattern discriminated.

2. An inspection apparatus for detecting existence or not of a defect on an inspected object in which an image of the inspected object irradiated by a light is picked by a video camera and a video signal therefrom is processed by an electronic processor comprising:
   a) a first means for setting up a pattern judging window on said inspected object to thereby judge whether or not there exists a pattern on said inspected object;
   b) a second means for setting up a plurality of inspection windows when it is judged that there is no pattern on said inspected object to thereby perform a predetermined defect inspection on portions of said inspected object within said plurality of inspection windows;
   c) a third means for setting up a pattern discrimination window on said inspected object when it is judged that there exists a pattern on said inspected object to thereby discriminate a kind of said pattern; and
   d) a fourth means for either setting up said inspection windows or another inspection window dependent on the kind of said pattern discriminated.

3. An inspection method for detecting existence or not of defects on an inspected object comprising the steps of:
   a) irradiating light on an inspected object, picking up the reflected or transmission light therefrom by a video camera for photoelectrical conversion and analyzing an image signal output from said video camera by an electronic processor;
   b) setting up a first window with a predetermined shape in an image picked up by said video camera at a predetermined position;
   c) conducting a first preset electronic processing for an image within said first window;
   d) setting up a plurality of second windows of preset positions and shapes for inspection on the inspected object based on the result of the first preset electronic processing conducted against the image within the first window;
   e) conducting a second preset electronic processing against an image within said second windows;
   f) setting a third window having a preset position and shape against the inspected object based on the first preset electronic processing results;
   g) conducting a third preset electronic processing against an image within said third window;
   based upon the results of said third electronic processing, either changing a part of said second window or setting up a fourth window, conducting a fourth preset electronic processing to an image within said fourth window based upon the results of said fourth electronic processing, either setting up said second window or setting up a fifth window in addition to said second window; and
   h) conducting a fifth preset electronic processing against an image within the said second window and/or fifth window, so that inspection of the existence or not of defects on the inspected object may be conducted.

4. An inspection method as claim in claim 3, wherein said second preset electronic processing is a defect detection processing.

5. An inspection method as claimed in claim 3, wherein said fifth window is an inspection window.

6. An inspection method as claimed in claim 3, wherein said fifth preset electronic processing is a defect detection processing.

7. An inspection method according to claim 3 further comprising the step of totally judging the results of said second and fifth preset electronic processings to detect whether or not there exist a defect.

8. An inspection method as claimed in claim 3, wherein said third window is a pattern judgement window for judging whether a pattern exists or not on the inspected object.

9. An inspection method as claimed in claim 8, wherein said third preset electronic processing is a brightness and darkness judgement processing.

10. An inspection method as claimed in claim 3, wherein said fourth window is a pattern discrimination window.

11. An inspection method as claimed in claim 10, wherein said pattern discrimination window is comprised of two windows.

12. An inspection method as claimed in claim 11, wherein said fourth preset electronic processing is brightness and darkness judgement and dimentional processings.

13. An inspection apparatus for detecting existence or not of defects on an inspected objects comprising:
   a) light source for irradiating an inspected object;
   b) a video camera picking up reflection or transmission light from said inspected object and for producing a video signal;
   c) an electronical processor for analyzing said video signal and setting up a first window having a preset place and shape against an image of the inspected object within an image as caught by said video camera;
   d) a first electronic processor for performing a first preset electronic processing against the image within said first window;

e) a first means for, based on the results of the first preset electronic processing conducted against an image within the said first window, setting up a plural number of second windows with preset shapes and places for inspection against the inspected object;

f) a second electronic processor for performing a second preset electronic processing against an image within the said second window;

g) a second means for, based on the results of the first preset electronic processing, setting up a third window with preset place and shape against said inspected object;

h) a third electronic processor for conducting a third preset electronic processing against an image within said third window;

i) a third means for, based on the results of said third electronic processor either changing a part of said second windows or setting up a fourth window;

j) a fourth electronic processor for conducting a fourth preset electronic processing against an image within the said fourth window;

k) a fourth means for, based on the results of said fourth electronic processing, either setting the said second windows or setting up a fifth window; and l) a fifth electronic processor for conducting a fifth electronic processing against an image within said second windows and/or fifth window to thereby detect whether or not there is a defect on the inspected object.

14. An inspection apparatus as claimed in claim 13, wherein said second preset electronic processing circuit is a defect detection processing circuit.

15. An inspection apparatus as claimed in claim 13, wherein said fourth window is a pattern discrimination window.

16. An inspection apparatus as claimed in claim 13, wherein said fifth window is an inspection window.

17. An inspection apparatus as claimed in claim 13, wherein said fifth preset electronic processing circuit is a defect detection processing circuit.

18. An inspection apparatus according to claim 13, further comprising defect existence inspection means which is conducted by feeding outputs from said second and fifth electronic processing circuits to a consolidated judgement circuit.

19. An inspection apparatus as claimed in claim 13, wherein said third window is a pattern judgement window for judging whether or not there is a pattern on the said inspected object.

20. An inspection apparatus as claimed in claim 19, wherein said third preset electronic processing circuit is a brightness and darkness judgement processing circuit.

21. An inspection apparatus as claimed in claim 20, wherein said pattern discrimination window is comprised of two windows.

22. An inspection apparatus as claimed in claim 21, wherein said fourth preset electronic processing circuit is a brightness and darkness judgement and dimentional processing circuit.

* * * * *